United States Patent
Palmieri et al.

(10) Patent No.: US 9,561,504 B2
(45) Date of Patent: Feb. 7, 2017

(54) MICROREACTOR WITH VENT CHANNELS FOR REMOVING AIR FROM A REACTION CHAMBER

(75) Inventors: Michele Palmieri, Agrate Brianza (IT); Gaetano Panvini, Catania (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 1144 days.

(21) Appl. No.: 12/648,226

(22) Filed: Dec. 28, 2009

(65) Prior Publication Data
US 2010/0167355 A1 Jul. 1, 2010

(30) Foreign Application Priority Data

Dec. 29, 2008 (IT) .............................. TO2008A0010

(51) Int. Cl.
*B01L 3/00* (2006.01)
*C12P 19/34* (2006.01)
*C12Q 1/68* (2006.01)

(52) U.S. Cl.
CPC .... *B01L 3/502707* (2013.01); *B01L 3/502723* (2013.01); *B01L 3/567* (2013.01); *C12P 19/34* (2013.01); *C12Q 1/686* (2013.01); *B01L 2200/0684* (2013.01); *B01L 2200/12* (2013.01); *B01L 2300/048* (2013.01); *B01L 2300/0816* (2013.01); *B01L 2300/0861* (2013.01); *B01L 2300/0874* (2013.01); *B01L 2300/1822* (2013.01); *B01L 2400/0406* (2013.01); *B01L 2400/0688* (2013.01)

(58) Field of Classification Search
CPC ................... B01L 2200/0684; B01L 3/502723
See application file for complete search history.

(56) References Cited

U.S. PATENT DOCUMENTS

| 6,001,307 | A | * | 12/1999 | Naka ....................... | B01L 3/502 |
| | | | | | 422/68.1 |
| 6,637,463 | B1 | * | 10/2003 | Lei ......................... | B01F 5/0403 |
| | | | | | 137/803 |
| 2004/0058408 | A1 | * | 3/2004 | Thomas et al. ................. | 435/32 |
| 2004/0248306 | A1 | | 12/2004 | Hernandez et al. | |

(Continued)

FOREIGN PATENT DOCUMENTS

WO      WO2007148358      12/2007

OTHER PUBLICATIONS

Goldschmidboeing, F., et al., Strategies for Void-Free Liquid-Filing of Micro Cavities, Transducers '05, The 13th International Conference on Solid-State Sensors, Actuators and Microsystems, Jun. 5-9, 2009, p. 1561-1564, Seoul, Korea.

(Continued)

*Primary Examiner* — Jonathan Hurst
(74) *Attorney, Agent, or Firm* — Seed IP Law Group LLP (57) ABSTRACT

A microreactor for performing chemical reactions, includes a body (2, 3), a first chamber (5) and a second chamber (7), both formed in the body (2,3). Interconnections (8) are provided for fluidly coupling the first chamber (5) and the second chamber (7) through the body (2, 3). The microreactor also includes a venting passage (10; 110; 210) formed in the body (2,3) and having a venting outlet (10b) in the second chamber (7) and at least one venting inlet (10a) in the first chamber (5), at a location where formation of bubbles is expected upon introduction of a liquid in the first chamber (5).

17 Claims, 5 Drawing Sheets

(56) References Cited

U.S. PATENT DOCUMENTS

2005/0229696 A1* 10/2005 Takayama ............. B01F 5/0646
73/204.26
2007/0264705 A1* 11/2007 Dodgson .................... 435/283.1
2008/0047322 A1* 2/2008 Harding et al. ............. 73/19.03

OTHER PUBLICATIONS

Goldschmidboeing, F., et al., Capillary Filing of Micro-Reservoirs with Various Cross Sections, Transducers '03, The 12$^{th}$ International Conference on Solid State Sensors, Actuators and Microsystems, Jun. 8-12, 2003, p. 1883-1886, Boston, MA.

* cited by examiner

MICROREACTOR WITH VENT CHANNELS FOR REMOVING AIR FROM A REACTION CHAMBER

CROSS-REFERENCE TO RELATED APPLICATIONS

This application claims priority to TO2008A001000 filed on Dec. 29, 2008, incorporated herein by reference in its entirety.

FEDERALLY SPONSORED RESEARCH STATEMENT

Not applicable.

REFERENCE TO MICROFICHE APPENDIX

Not applicable.

FIELD OF THE INVENTION

The present invention relates to a microreactor with vent channels for removing air from a reaction chamber.

BACKGROUND OF THE INVENTION

Typical procedures for analyzing biological materials, such as nucleic acid, protein, lipid, carbohydrate, and other biological molecules, involve a variety of operations starting from raw material. These operations may include various degrees of cell separation or purification, cell lysis, amplification or purification, and analysis of the resulting amplification or purification product.

As an example, in DNA-based blood analyses samples are often purified by filtration, centrifugation or by electrophoresis so as to eliminate all the non-nucleated cells, which are generally not useful for DNA analysis. Then, the remaining white blood cells are broken up or lysed using chemical, thermal or biochemical means in order to liberate the DNA to be analyzed. Next, the DNA is denatured by thermal, biochemical or chemical processes and amplified by an amplification reaction, such as PCR (polymerase chain reaction), LCR (ligase chain reaction), SDA (strand displacement amplification), TMA (transcription-mediated amplification), RCA (rolling circle amplification), and the like. The amplification step allows the operator to avoid purification of the DNA being studied because the amplified product greatly exceeds the starting DNA in the sample.

If RNA is to be analyzed the procedures are similar, but more emphasis is placed on purification or other means to protect the labile RNA molecule. RNA is usually copied into DNA (cDNA) and then the analysis proceeds as described for DNA.

Finally, the amplification product undergoes some type of analysis, usually based on sequence or size or some combination thereof In an analysis by hybridization, for example, the amplified DNA is passed over a plurality of detectors made up of individual oligonucleotide detector fragments that are anchored, for example, on electrodes. If the amplified DNA strands are complementary to the oligonucleotide detectors or probes, stable bonds will be formed between them (hybridization). The hybridized detectors can be read by observation using a wide variety of means, including optical, electromagnetic, electromechanical or thermal means.

Other biological molecules are analyzed in a similar way, but typically molecule purification is substituted for amplification, and detection methods vary according to the molecule being detected. For example, a common diagnostic involves the detection of a specific protein by binding to its antibody. Such analysis requires various degrees of cell separation, lysis, purification and product analysis by antibody binding, which itself can be detected in a number of ways. Lipids, carbohydrates, drugs and small molecules from biological fluids are processed in similar ways. However, we have simplified the discussion herein by focusing on nucleic acid analysis, in particular DNA analysis, as an example of a biological molecule that can be analyzed using the devices of the invention.

Some devices integrate more than one process step. For example, some devices are designed to accept biological samples previously prepared and to perform amplification and detection processes (that may involve denaturation, hybridization of target probes and reading of the probes).

In most cases, individual operations are carried out in separate chambers. So, there is a need to transfer partially processed samples from one chamber to another and, to this end, microfluidic connections are provided between subsequent chambers.

However, handling small volumes of liquids, such as required for biochemical analyses (in the range of few microliters) can be difficult, especially when capillary forces are involved. In fact, air bubbles may easily be encapsulated in a chamber when a sample is loaded into a microreactor. Essentially, the geometry of the chambers and the affinity of the sample with the material which the chambers are made of may produce very instable menisci when the chambers are filled with a liquid. The edges of the menisci may join in certain conditions and air bubbles can be entrapped within the liquid.

A single air bubble may occupy a relatively large fraction of the chamber, in view of its small volume (some microliters) and cause leakage toward another chamber through the microfluidic connections. In other words, a volume of the sample may be pushed away by the air bubble and may escape from the reaction chamber through the microfluidic connections. The analysis may be compromised, because important process parameters, such as volume, balance of reagents, pressure, temperature, are affected by the bubble. In any case, a lower amount of sample is available for processing.

The object of the invention is to provide chemical microreactor and a method for carrying out a chemical reaction that are free from the above described limitations.

SUMMARY OF THE INVENTION

According to the present invention, a microreactor and a method for carrying out a chemical reaction are provided as claimed.

BRIEF DESCRIPTION OF THE DRAWINGS

For the understanding of the present invention, some embodiments thereof will be now described, purely as non-limitative examples, with reference to the enclosed drawings, wherein.

DETAILED DESCRIPTION OF THE INVENTION

FIGS. 1-4 show one embodiment of a microreactor, indicated by the reference number 1. The microreactor 1 is formed in a semiconductor body including a first chip 2 and a second chip 3, bonded together through a bonding layer 4. The microreactor 1 comprises reaction chambers 5 (two, in the embodiment herein described) and a detection chamber 7, all accommodated in the first chip 2 and delimited at their bottom by the second chip 3. Moreover, the microreactor 1 comprises fluidic capillary interconnections 8 and at least one vent passage, defined by a vent channel 10 in this embodiment, for fluidly coupling the reaction chambers 5 with the detection chamber 7. In this embodiment, in particular, the microreactor 1 comprises one vent channel 10 for each reaction chamber 5.

Figure 1:
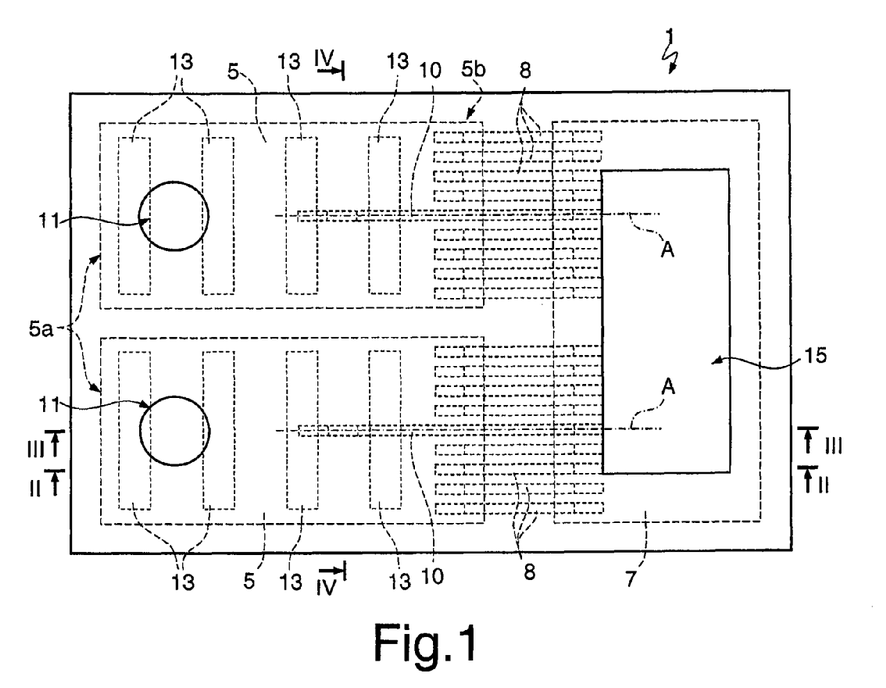
FIG. 1 is a top plan view of a microreactor according to one embodiment of the present invention.
Figure 2:
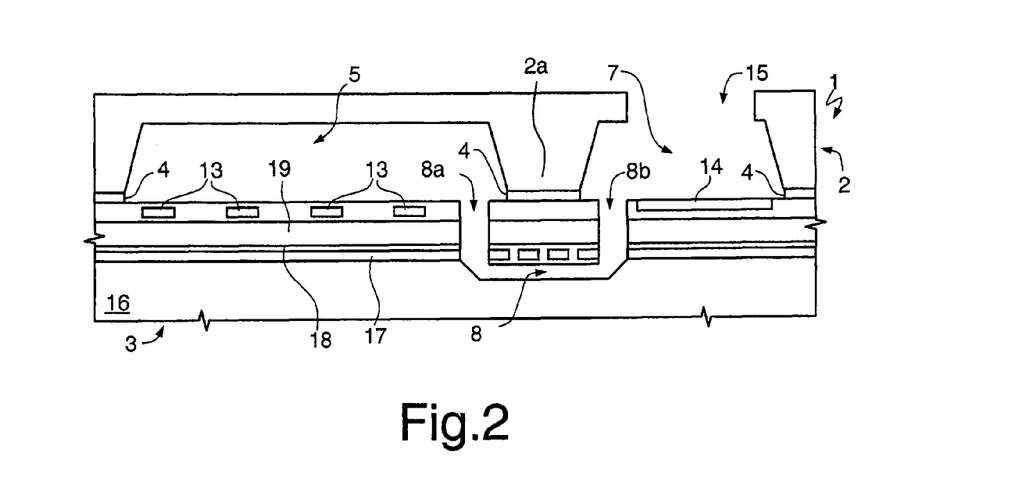
FIG. 2 is a cross-sectional view of the microreactor of FIG. 1, taken along the line II-II of FIG. 1.
Figure 3:
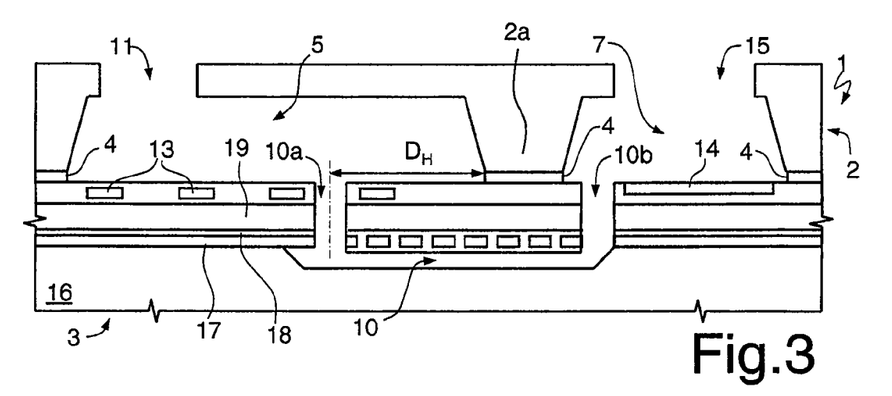
FIG. 3 is a cross-sectional view of the microreactor of FIG. 1, taken along the line III-III of FIG. 1.
Figure 4:
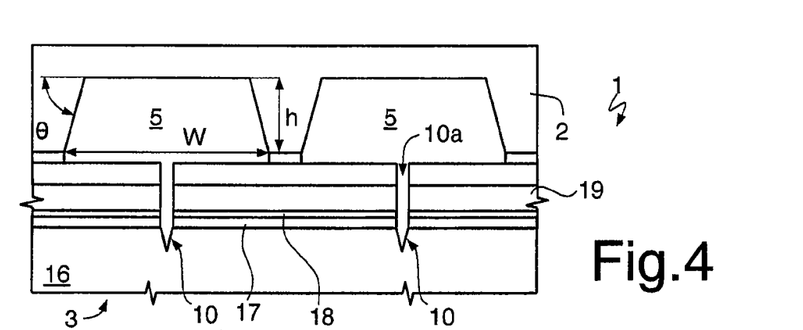
FIG. 4 is a cross-sectional view of the microreactor of FIG. 1, taken along the line IV-IV of FIG. 1.

In one embodiment, the reaction chambers are designed to perform a nucleic acid amplification process, such as PCR. It is however understood that the number of the reaction chambers 5 may be different, i.e. one as well as more than two, and that different reactions may be carried out. The reaction chambers 5, which in this embodiment have substantially the same shape, are in the form of microfluidic channels, elongated and rectangular in top plan view, and having trapezoidal cross-sections transverse to their longitudinal axes A, as illustrated in FIG. 4. The reaction chambers 5 are arranged adjacent to one another along respective greater sides, while smaller sides are adjacent to the detection chamber 7. Reaction chambers 5 are accessible from outside through respective apertures 11 at proximal ends 5a thereof.

The second chip 3 incorporates heaters 13 at the bottom of the reaction chambers 5 and thermally coupled thereto. Heaters 13 are resistors connectable to an external control unit and to a power source (here not shown and schematically illustrated in FIG. 10) for controllably delivering heat into the reaction chambers 5, in accordance with a desired reaction temperature profile. In one embodiment, the reaction chambers 5 are provided with separate and independently controllable heaters 13.

In the embodiment herein described, the detection chamber 7 accommodates a microarray 14 of nucleic acid probes, arranged on the second chip 3. The probes include individual oligonucleotide detector fragments that are anchored, for example, on electrodes or directly on the chip 3 and are available for hybridization with complementary strands that may be contained in a sample processed by the microreactor 1. However, in other embodiments, the oligonucleotide detector fragments may be added directly to the sample, instead of using a microarray of probes, and other detection means are also possible.

An optional inspection window 15 is provided through the first chip 2, so that the detection chamber 7, namely the microarray 14, is visible from outside the microreactor 1.

As already mentioned, the reaction chambers 5 are fluidly coupled to the detection chamber 7 through the capillary interconnections 8 and the vent channels 10, all of which are made in the second chip 3 in the embodiment herein described. More precisely, the capillary interconnections 8 and the vent channels 10 have respective buried portions, accommodated in a semiconductor substrate 16 of the second chip 3 (e.g. of monocrystalline silicon), and communicate with the reaction chambers 5 through respective inlets 8a, 10a and with the detection chambers through respective outlets 8b, 10b. Inlets 8a, 10a and outlets 8b, 10b extend perpendicular to the buried portions of the capillary interconnections 8 and of the vent channels 10, through several layers of the second chip 3, that may include a hard mask layer 17, an oxide layer 18 and a pseudo-epitaxial layer 19, e.g. of polysilicon. The hard mask layer 17 in turn may be a multi-layer stack, including e.g. a silicon carbide layer and a silicon nitride layer, which are not individually illustrated in the drawings.

In this embodiment, the inlets 8a of the capillary interconnections 8 are arranged at distal ends 5b of the respective reaction chambers, opposite to the proximal ends 5a where the apertures 11 are formed. The position of the inlets 8a is such that a sample loaded in the reaction chambers 5 can be completely evacuated through the capillary interconnections 8 by applying a pressure at the apertures 11.

In one embodiment, there are eight capillary interconnections 8 in each reaction chamber 5, uniformly distributed on both sides of respective vent channels 10.

Buried portions of the vent channels 10 extend along longitudinal axes A of the respective detection chambers 5 and run below a wall portion 2a of the first chip 2, that separates the reaction chamber 5 from the detection chamber 7. The inlets 10a extend perpendicular to the buried portions of the respective vent channels 10 and are spaced a distance apart from the inlets 8a of the capillary interconnections 8, along the longitudinal axes A of the respective reaction chamber 5.

The location of the inlets 10a of the vent channels 10 is determined based on the geometry of the reaction chambers. Namely, the inlets 10a of the vent channels 10 are formed at regions where formation of bubbles is expected upon introduction of a volume of a liquid sample approximately equal to the volume of the reaction chambers 5. The formation of bubbles in a liquid sample within small chambers is in fact affected by the geometry of the chambers and by the affinity between the liquid and the walls defining the chambers. Since the fundamental components of the sample to be loaded in the microreactor 1 (e.g. aqueous sample) are known in advance, the areas of the reaction chambers 5 where bubbles are most likely to form can be determined with satisfactory approximation. In one embodiment, the inlets 10a of the vent channel 10 are located at distance from the distal ends 5b of the reaction chambers 5 that is about one hydraulic equivalent diameter $D_H$. The hydraulic equivalent diameter $D_H$ is the diameter of a cylindrical vessel with the same cross-sectional area. In the example described (see FIG. 4), the cross section is trapezoidal (isosceles) and the hydraulic equivalent diameter $D_H$ is given by:

$$D_H = \frac{2(W\tan\theta - h)h}{W\tan\theta + h(1/\cos\theta - 1)}$$

where W and h are respectively the width and the height of the cross-section and θ is the angle formed by the prolongation of the smaller base and one side of the trapezoidal cross-section. The thickness of the bonding layer 4 may be neglected for the purpose of determining the equivalent hydraulic diameter $D_H$.

In one embodiment herein described, the buried portions of the vent channels 10 extend somewhat beyond the respective inlets 10a. Thus, the cross-section of the fluidic passages changes abruptly at the end of the inlets 10a, so that an overpressure is required to move a liquid further along the vent channels 10. In other words, capillary "stop valves" are defined at the end of the inlets 10a of the vent channels 10, namely at intersections of the inlets 10a with the buried portions of the vent channels 10.

Figure 5:
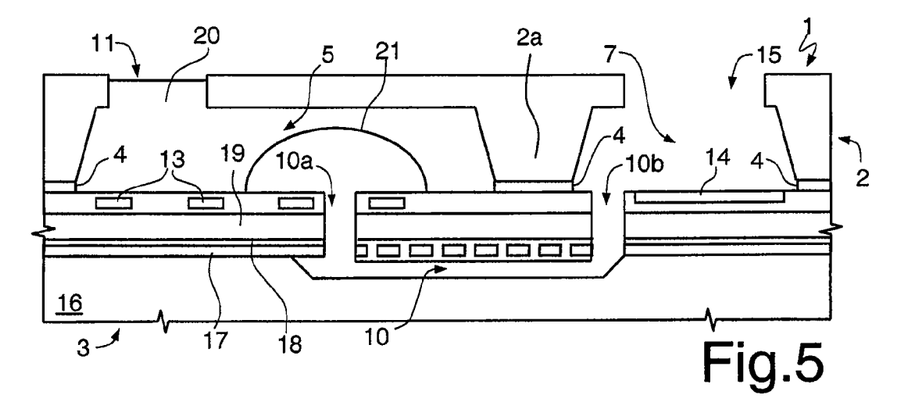
FIG. 5 show the same view as FIG. 3, in a first operating condition.
Figure 6:
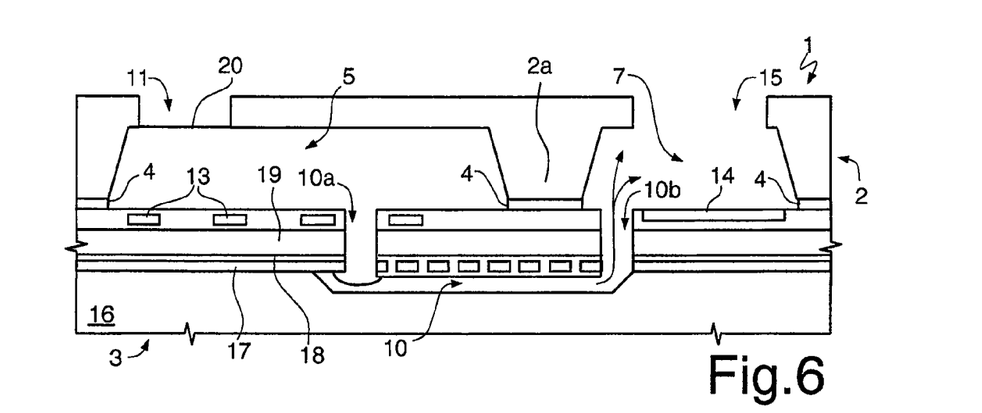
FIG. 6 show the same view as FIG. 3, in a second operating condition.

FIGS. 5 and 6 illustrate a step of loading a liquid sample 20 into the microreactor 1 for processing.

The sample 20 is dispensed through the apertures 11 of the reaction chambers 5 e.g. by manually controlled or servo-actuated micro-pipettes (not shown). Normally, the volume of sample delivered is approximately the same as the volume of the reaction chambers 5 (e.g. 10 to 20 82 l).

As well known in microfluidics, air bubbles can be encapsulated in a liquid medium in capillary filling of microchannels or microreservoirs, depending on the balance between capillary forces that suck the fluid, and viscous forces that retard the flow. In some cases, very instable menisci may form and lead to bubble encapsulation.

FIG. 5 schematically shows an air bubble 21 encapsulated in a reaction chamber 5 while the microreactor 1 is filled. Due to the position of the inlet 10a, the air bubble 21 communicates with the detection chamber 7 through the vent channel 10. Thus, air is evacuated from the reaction chamber 5 and flows towards the detection chamber 7, as illustrated in FIG. 6.

A small amount of the liquid sample 20 may be sucked through the inlets 10a of the vent channels 10. However, sucked fluid is arrested at the end of the inlets 10a, due to the "stop valve" effect. Accordingly, leakage of liquid sample 20 is generally prevented.

The vent channel 10 allows to remove air bubbles that may be encapsulated in the reaction chamber 5 and assures that the desired volume of sample is actually processed. The whole volume of the reaction chambers 5 is in fact occupied by the sample 20 and leakage toward the detection chamber 7, that could be caused by air bubbles, is avoided.

The sample 20 may be transferred to the detection chamber 7 through the capillary interconnections 8 by applying a pressure at the apertures 11 of the reaction chambers 5. Since the inlets 8a of the capillary interconnections 8 are located at the distal end 5b of the respective reaction chambers 5, the reaction chambers 5 may be completely cleared.

The microreactor 1 does not need to incorporate any moving part or element. Even the function of arresting liquid sucked through the vent channels 10 is simply implemented by the capillary stop valve at the intersection of the inlet 10a and the buried portion of the vent channel 10. The capillary stop effect is in fact sufficient to block the flow before the sample 20 reaches the detection chamber 7. Thus, only a negligible volume of liquid is sucked through the vent channel 10 and the sample 20 is virtually completely available for amplification (in this embodiment, while in other embodiments different reactions may be carried out in the reaction chamber 5).

The microreactor 1 may be made by separately processing two semiconductor wafers. A first semiconductor wafer is selectively etched to form the reaction chambers 5 and the detection chamber 7. Then, the back face of the first wafer is thinned out by a mechanical or mechanical-chemical process and subsequently the apertures 11 and the window 15 are opened.

The capillary interconnections 8 and the vent channels 10 are formed in a second semiconductor wafer. In one embodiment, the hard mask layer 17 is deposited on the substrate 16 and a hard mask is made therefrom above a region intended to accommodate the capillary interconnections 8 and the vent channels 10. The hard mask may be in the form of a grid with microapertures. The substrate 16 is etched through the hard mask that remains suspended above cavities. A thin layer of polysilicon is deposited and oxidized, to form the oxide layer 18 that covers the hard mask layer 17 and incorporates the hard mask. Then, a polysilicon seed layer is deposited and the pseudo-epitaxial layer 19 is grown therefrom. After depositing a dielectric layer, the heaters 13 and the microarray 14 are made.

The first wafer and the second wafer are finally bonded to one another and cut into dice, each including one microreactor 1.

Figure 7:
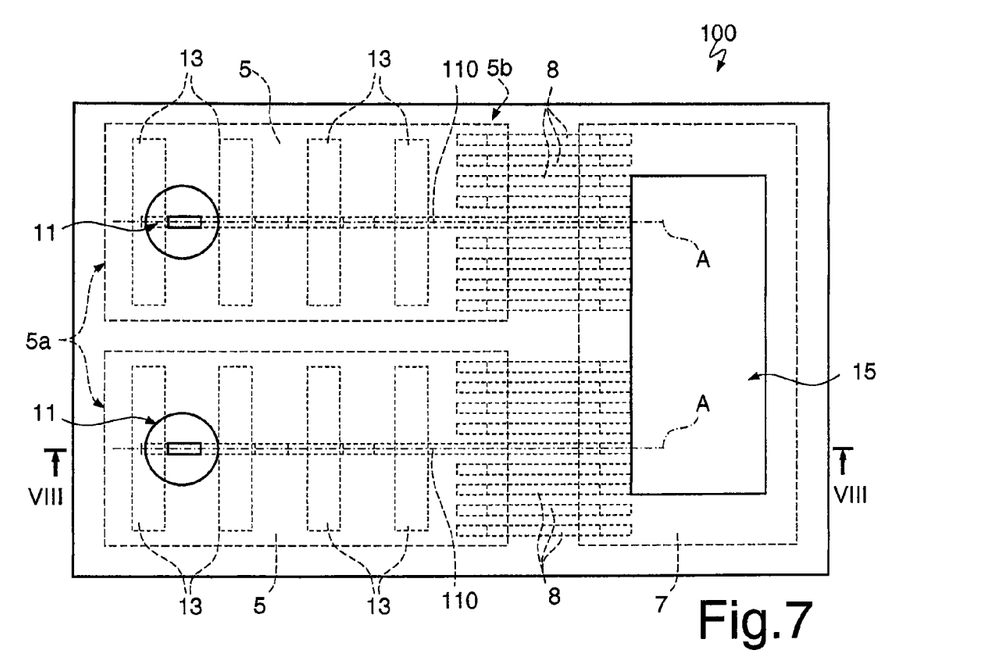
FIG. 7 is a top plan view of a microreactor according to another embodiment of the present invention.
Figure 8:
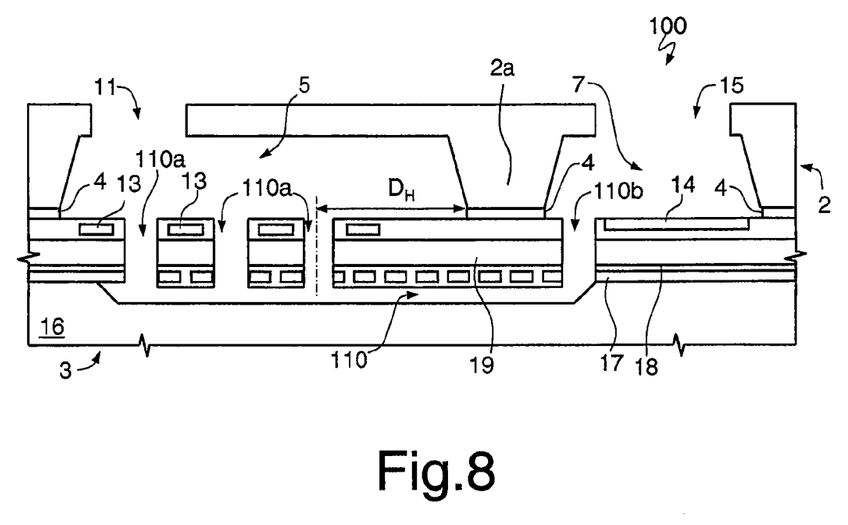
FIG. 8 is a cross-sectional view of the microreactor of FIG. 7, taken along the line VIII-VIII of FIG. 1.

According to another embodiment, illustrated in FIGS. 7 and 8, a microreactor 100 comprises the reaction chambers 5, the detection chamber 7, the capillary interconnections 8 and at least one vent channel 110 for each of the reaction chambers 5. Heaters 13 and a microarray 14 are arranged in the reaction chambers 5 and in the detection chamber 7, respectively. The vent channels 110 extend along longitudinal axes A of the respective reaction chambers 5, from near the proximal end 5a to the detection chamber 7, and have a plurality of inlets 110a in the reaction chambers 5, at regions where the formation of air bubbles is expected. In particular, the inlets 110a are arranged at respective distances from the distal end 5b and are uniformly spaced along the vent channels 110, that communicate with the detection chamber 7 through respective outlets 110b.

Figure 9:
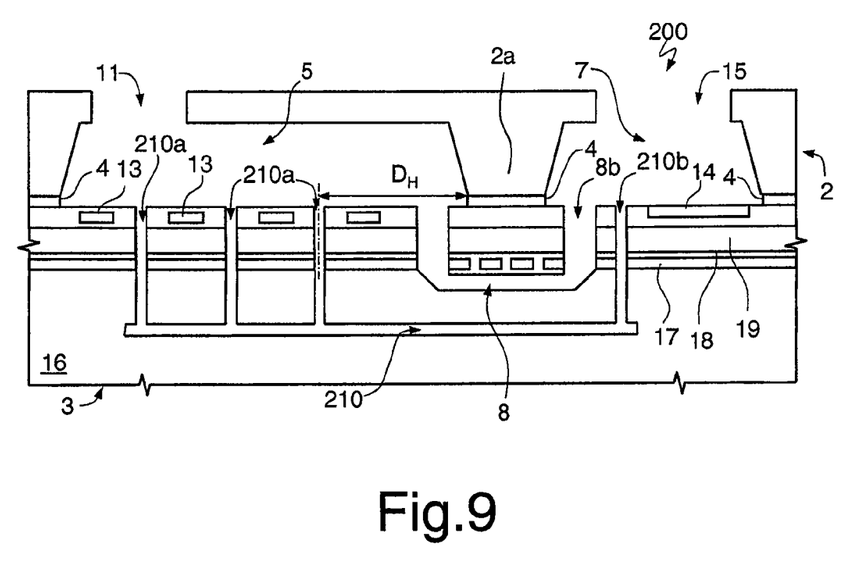
FIG. 9 is a cross-sectional view through a microreactor according to still another embodiment of the present invention.

According to another embodiment, shown in FIG. 9, in a microreactor 200, vent channels 210 extend from respective reaction chambers 5 to the detection chamber 7 and run below the capillary interconnections 8, i.e. deeper in the second chip 3. Also in this case, the vent channels 210 extend from near the proximal end 5a of the reaction chambers to the detection chamber 7 and the inlets 210a are uniformly spaced along the vent channels 210, while outlets 210b communicate with the detection chamber 7.

In the microreactor 200, the vent channels 210 may be made by incorporating a sacrificial region, e.g. of silicon dioxide, in an epitaxial layer before starting the process steps for manufacturing the capillary interconnections 8 and the vent channels 10. Later, the inlets 210a are opened and used to remove the sacrificial region.

Figure 10:
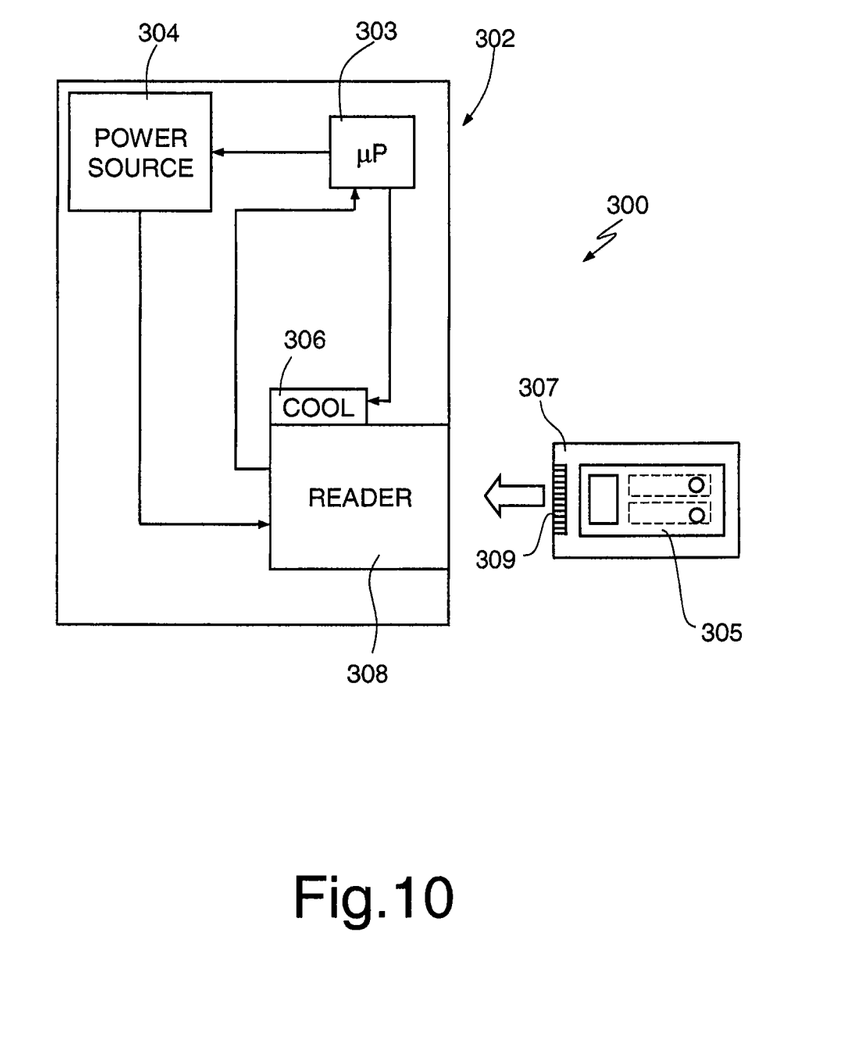
FIG. 10 is a system depiction of an chemical analyses apparatus according to one embodiment of the present invention.

With reference to FIG. 10, a biochemical analysis apparatus 300 comprises a computer system 302, including a processing unit 303, a power source 304 controlled by the processing unit (μP) 303, and a microreactor 305, having the structure and operation already described. The microreactor 305 is mounted on a board 307, together making a disposable cartridge that is removably inserted in a reader device 308 of the computer system 302, for selective coupling to the processing unit 303 and to the power source 304. To this end, the board 307 is also provided with an interface 309.

Heaters on the microreactor 305 (not shown) are coupled to the power source 304 through the interface 309. The reader device 308 can also include a cooling element 306, e.g. a Peltier module or a fan coil, which is controlled by the processing unit 303 and is thermally coupled to the microreactor 305 when the board 307 is loaded in the reader device 308.

Finally, it is clear that numerous modifications and variations may be made to the device and the method described and illustrated herein, all falling within the scope of the invention, as defined in the attached claims.

In particular, the number, shape and placement of the reaction and detection chambers is not limited to the example described. Likewise, the number, shape and placement of the capillary interconnections and vent channels could be different.

What is claimed is:

1. A microreactor for performing chemical reactions, comprising:
    a body;
    an elongated microfluidic first chamber having a top and a bottom and first and second sides formed in the body, the first sides extending along a length of the first chamber between a first end and a second end of the first chamber and the second sides extending along a width of the first chamber, the length being greater than the width;
    a second chamber formed in the body, the first chamber having a fluid inlet on said top at the first end of the first chamber and the second end of the first chamber chamber being nearer than the first end to the second chamber;
    interconnections that fluidly couple the first chamber and the second chamber through the body, the interconnections having interconnection inlets through said bottom at the second end of the first chamber,; and
    a vent passage formed in the body and having a vent outlet in the second chamber and at least one vent inlet through the bottom of the first chamber, at a location between the fluid inlet and the interconnection inlets along the length of the first chamber, wherein the first chamber has a hydraulic equivalent diameter (DH) and the vent inlet is located at a distance of about one hydraulic equivalent diameter (DH) from the second end.

2. The microreactor of claim 1, wherein the first chamber has a trapezoidal cross-section and the hydraulic equivalent diameter (DH) is given by $$D_H = \frac{2(W\tan\theta - h)h}{W\tan\theta + h(1/\cos\theta - 1)}$$

where W and h are respectively a width and a height of the trapezoidal cross-section of the reaction chamber and θ is an angle formed by a prolongation of a smaller base and one side of the trapezoidal cross-section of the reaction chamber.

3. The microreactor of claim 1, wherein the vent passage has a plurality of vent inlets in the first chamber.

4. The microreactor of claim 3, wherein the vent inlets are uniformly spaced along the vent passage.

5. The microreactor of claim 1, wherein:
    the body comprises a first chip and a second chip, bonded to one another;
    the first chamber and the second chamber are formed in the first chip and delimited on one side by the second chip; and
    the vent passage includes a microfluidic channel formed in the second chip.

6. The microreactor of claim 5, wherein the vent passage has a buried portion accommodated in the second chip and the vent inlet extends perpendicular to the buried portion of the vent passage.

7. The microreactor of claim 6, wherein an intersection of the vent inlet and of the buried portion of the vent passage is configured to define a capillary stop valve for a first fluid and the interconnections are configured to transfer the first fluid from the first chamber to the second chamber.

8. The microreactor of claim 1, comprising heaters thermally coupled to the first chamber and connectable to an external power source for controllably delivering thermal power into the first chamber.

9. The microreactor of claim 1, comprising a microarray of nucleic acid probes, accommodated in the second chamber.

10. A chemical analysis apparatus comprising
    a microreactor;
    a processing unit;
    a power source controlled by the processing unit;
    a reader device, for receiving the microreactor and coupling the microreactor to the power source;
    wherein the microreactor includes:
        a body;
        an elongated microfluidic first chamber having a top and a bottom and first and second sides formed in the body, the first sides extending along a length of the first chamber between a first end and a second end of the first chamber and the second sides extending along a width of the first chamber, the length being greater than the width;
        a second chamber formed in the body, the first chamber having a fluid inlet through said top at the first end of the first chamber and the second end of the first chamber being nearer than the first end to the second chamber;
        interconnections that fluidly couple the first chamber and the second chamber through the body, the interconnections having interconnection inlets through the bottom at a second end of the first chamber,; and
        a vent passage formed in the body and having a vent outlet in the second chamber and at least one vent inlet on the bottom of the first chamber, at a location between the fluid inlet and the interconnection inlets along the length of the first chamber, wherein the first chamber has a hydraulic equivalent diameter (DH) and the vent inlet is located at a distance of about one hydraulic equivalent diameter (DH) from the second end.

11. The chemical analysis apparatus of claim 10, wherein the first chamber has a trapezoidal cross-section and the hydraulic equivalent diameter (DH) is given by $$D_H = \frac{2(W\tan\theta - h)h}{W\tan\theta + h(1/\cos\theta - 1)}$$

where W and h are respectively a width and a height of the trapezoidal cross-section of the reaction chamber and θ is an angle formed by a prolongation of a smaller base and one side of the trapezoidal cross-section of the reaction chamber.

12. The chemical analysis apparatus of claim 10, wherein:
the body comprises a first chip and a second chip, bonded to one another;
the first chamber and the second chamber are formed in the first chip and delimited on one side by the second chip; and
the vent passage includes a microfluidic channel formed in the second chip.

13. The chemical analysis apparatus of claim 10, comprising a microarray of nucleic acid probes, accommodated in the second chamber.

14. A microreactor for performing chemical reactions, comprising:
a body;
a first chamber and a second chamber, formed in the body;
interconnections for fluidly coupling the first chamber and the second chamber through the body, said interconnections having inlets in the first chamber and outlets in the second chamber; and
a vent passage formed in the body and having at least one vent inlet in the first chamber and having a vent outlet in the second chamber, wherein:
the first chamber has a first end and a second end along a length of said first chamber, the second end of the first chamber being nearer than the first end to the second chamber;
the first chamber includes a fluid inlet at said first end and interconnection inlets at the second end of said first chamber;
the vent inlet is between said fluid inlet and said interconnection inlets on said length;
the vent passage has a buried portion and the vent inlet extends perpendicular to the buried portion of the vent passage;
an intersection of the vent inlet and the buried portion of the vent passage is configured to define a capillary stop valve; and
the first chamber has a hydraulic equivalent diameter (DH) and the vent inlet is located at a distance of about one hydraulic equivalent diameter (DH) from the second end.

15. The microreactor of claim 14, wherein the first chamber has a trapezoidal cross-section and the hydraulic equivalent diameter (DH) is given by $$D_H = \frac{2(W\tan\theta - h)h}{W\tan\theta + h(1/\cos\theta - 1)}$$

where W and h are respectively a width and a height of the trapezoidal cross-section of the reaction chamber and θ is an angle formed by a prolongation of a smaller base and one side of the trapezoidal cross-section of the reaction chamber.

16. The microreactor of claim 14, wherein:
the body comprises a first chip and a second chip, bonded to one another;
the first chamber and the second chamber are formed in the first chip and delimited on one side by the second chip; and
the vent passage includes a microfluidic channel formed in the second chip.

17. The microreactor of claim 14, comprising a microarray of nucleic acid probes, accommodated in the second chamber.

* * * * *

UNITED STATES PATENT AND TRADEMARK OFFICE
CERTIFICATE OF CORRECTION

PATENT NO. : 9,561,504 B2
APPLICATION NO. : 12/648226
DATED : February 7, 2017
INVENTOR(S) : Michele Palmieri et al.

It is certified that error appears in the above-identified patent and that said Letters Patent is hereby corrected as shown below:

In the Claims

Column 7, Lines 30-32:
"chamber and the second end of the first chamber chamber being nearer than the first end to the second chamber;" should read, --chamber and the second end of the first chamber being nearer than the first end to the second chamber;--.

Signed and Sealed this
Second Day of May, 2017

Michelle K. Lee
*Director of the United States Patent and Trademark Office*